(12) United States Patent
Brodaczewski et al.

(10) Patent No.: US 11,432,823 B2
(45) Date of Patent: Sep. 6, 2022

(54) LIGATING CLIP CARTRIDGE

(71) Applicant: Grena USA LLC, Wilmington, DE (US)

(72) Inventors: Wieslaw Mieczyslaw Brodaczewski, Brentfoord (GB); Andrzej Janusz Decewicz, Nottingham (GB); Tomasz Przekopiński, Zabki (PL)

(73) Assignee: Grena USA LLC, Wilmington, DE (US)

( * ) Notice: Subject to any disclaimer, the term of this patent is extended or adjusted under 35 U.S.C. 154(b) by 626 days.

(21) Appl. No.: 16/513,834

(22) Filed: Jul. 17, 2019

(65) Prior Publication Data
US 2021/0015486 A1 Jan. 21, 2021

(51) Int. Cl.
A61B 17/122 (2006.01)
A61B 17/00 (2006.01)

(52) U.S. Cl.
CPC .. A61B 17/1222 (2013.01); A61B 2017/0053 (2013.01)

(58) Field of Classification Search
CPC ........ A61B 17/1222; A61B 2017/0053; A61B 17/12; A61B 17/122
USPC .................. 206/438; 606/142, 144, 148, 139
See application file for complete search history.

(56) References Cited

U.S. PATENT DOCUMENTS

| | | | |
|---|---|---|---|
| 4,972,949 A | 11/1990 | Peiffer | |
| 5,046,611 A | 9/1991 | Oh | |
| 5,201,416 A | 4/1993 | Taylor | |
| 5,279,416 A | 1/1994 | Malee | |
| 6,419,682 B1 | 7/2002 | Appleby | |
| 6,880,699 B2 | 4/2005 | Gallagher | |
| 8,839,954 B2 | 9/2014 | Disch | |
| 2004/0040875 A1* | 3/2004 | Gallagher | A61B 17/1222 206/399 |
| 2009/0152147 A1 | 6/2009 | Cannady | |
| 2013/0161216 A1* | 6/2013 | Disch | B65D 85/24 206/339 |
| 2017/0027576 A1 | 2/2017 | Castro | |

FOREIGN PATENT DOCUMENTS

| | | |
|---|---|---|
| EP | 0314064 B1 | 12/1994 |
| EP | 0482861 B1 | 3/1997 |

* cited by examiner

Primary Examiner — Tan-Uyen T Ho
Assistant Examiner — Bridget E. Rabaglia
(74) Attorney, Agent, or Firm — Seth Natter; Haug Partners LLP

(57) ABSTRACT

A cartridge for ligating clips includes compartments formed of partitions lying in spaced parallel planes and a stringer spanning between the partitions. The legs of a clip are joined at a hinge which is seated over the stringer. The stringer comprises a substantially cylindrical body and a depending narrow support flange. Opposed faces of adjacent partitions include areas of reduced thickness spaced apart a distance sufficient to permit limited pivotal movement of the clip about the stringer. An abutment edge of the partition face provides a stop which is engaged by bosses at the ends of the clip legs to limit pivotal movement of the clip legs and prevent ribs of the clip from engaging the stringer.

20 Claims, 6 Drawing Sheets

LIGATING CLIP CARTRIDGE

BACKGROUND OF THE INVENTION

1. Field of the Invention

This invention relates generally to packaging, storing, shipping and dispensing of pronged polymeric ligating clips and more specifically to an improved clip cartridge which maintains clip prongs or ribs free of contact with cartridge support structures when loading clips into the cartridge as well as during storage, transport and subsequent extraction.

2. Antecedents of the Invention

Many surgical procedures require vessels or other tissues of the human body to be ligated during the surgical procedure. For example, many surgical procedures require cutting blood vessels (e.g., veins or arteries), and these blood vessels may require ligation to stop bleeding. In some instances, a surgeon may wish to ligate the vessel temporarily to reduce blood flow to the surgical site during the surgical procedure. In other instances a surgeon may wish to permanently ligate a vessel.

Ligation of vessels or other tissues have been performed by closing the vessel with a ligating clip, or by suturing the vessel with surgical thread. The use of surgical thread for ligation required complex manipulations of the needle and suture material to form the knots required to secure the vessel. Such complex manipulations were time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries. Typically, a clip is applied to the vessel or other tissue by using a dedicated mechanical instrument commonly referred to as a surgical clip applier instrument, ligating clip applier, or hemostatic clip applier. Generally, the clip is left in place after application to the vessel. With some clips, if applied in an inappropriate location, the clip is removed by using a separate instrument dedicated for that purpose, i.e., a clip removal instrument.

Asymmetric polymeric clips have been disclosed in U.S. Pat. Nos. 4,834,096, 5,062,846 and 10,265,079 which patents are incorporated herein in their entireties by reference.

These polymeric clips generally comprise a pair of curved legs joined at their proximal ends with an integral hinge. The distal ends of the curved legs include interlocking latching members. For example, with reference to FIG. 1 of U.S. Pat. No. 10,265,079, the distal end of one leg includes a lateral boss adjacent a hook. The hook latches between a pair of bosses at the distal end of the other leg to lock the clip in a closed ligating position.

The inner face of the one leg is concave while the inner face of the other leg is convex. The inner faces of both legs include a plurality of prongs or ribs for enhanced gripping of the vessel or tissue to be ligated during a surgical procedure.

A clip applier instrument specifically designed for asymmetric plastic clips is used to close the clip around the tissue to be ligated and to lock the clip in the closed condition. During a surgical procedure requiring vessel ligation, the jaws of the clip applier instrument are actuated into compressing contact with the bosses. This causes the legs to pivot inwardly toward one another about the hinge, until the hook of the one leg latches between the pair of bosses at the distal end of the other leg, compressing the vessel between the legs. Clip applier instruments configured for use with asymmetric polymeric clips are disclosed in U.S. Pat. Nos. 5,100,416 and 6,880,699 which are incorporated herein by reference.

Because the asymmetric polymeric clips are small and several clips are often used in a surgical procedure, holding devices are employed to store and retain the clips between the time of their manufacture and packaging and ultimate use during a surgical procedure. Numerous clip cartridges have been developed an example of which is disclosed in U.S. Pat. No. 6,880,699.

U.S. Pat. No. 6,880,699 discloses a cartridge comprising a plurality of compartments within a tray. The compartments are defined by a plurality of transverse partition walls facing one another. As illustrated in FIG. 8 of U.S. Pat. No. 6,880,699, a clip supporting post projects upwardly from a base of the cartridge and spans between the partition walls.

The hinge portion of a clip is seated over an apex of the post, however, as illustrated in the drawings of U.S. Pat. No. 6,880,699, depending from the apex, the post is configured with a convex side portion, shown on the right side of the post in FIG. 6 and on the left side of the post in FIG. 8. The post is also configured with a concave side portion, shown on the left side of the post in FIG. 6 and on the right side of the post in FIG. 8. The convex and concave side portions are subject to engagement against the ribs projecting from the inner faces of the legs, as illustrated in FIG. 8 of U.S. Pat. No. 6,880,699.

Significantly, such engagement occurs under compressive force when the legs are urged toward one another under the force of the clip applier instrument during extraction of the clip from the cartridge. As such, ribs or prongs are prone to becoming blunted and sharp edges, intended to engage vessels or tissue to be ligated, may become dull and deformed with concomitant reduced efficacy. Such engagement may also occur as a result of cartridge movement during storage, transport or shipment.

SUMMARY OF THE INVENTION

In compendium, the invention comprises a cartridge having parallel transverse partitions which define compartments for polymeric ligating clips. The clips include a pair of curved legs having ribs or prongs on their inner faces. The legs are joined at a hinge, with transverse bosses at or adjacent the distal end of each leg. The hinge is seated over a stringer which spans between the partitions. The stringer comprises a substantially cylindrical body having a radius equal to or slightly less than the internal radius of the hinge when the clip is open. A depending support flange extends from the bottom of the stringer body, whereby the stringer is configured with a keyhole shaped cross section.

Opposed faces of adjacent partitions include lateral portions of reduced thickness which are spaced apart a distance sufficient to permit limited pivotal movement of the clip about the stringer. Thicker intermediate face portions define a narrow constricted zone of each compartment. An abutment edge transitions between the lateral portions and the intermediate portions to provide stops which are engaged by the bosses at the ends of the clip legs to block pivotal movement of the ends of the clip legs into the constricted zone and contact between the ribs or prongs and the stringer.

The abutment edge restrains bending of the legs into the constricted zone upon extraction from the cartridge, thereby assuring that the ribs or prongs of the clip will not become dull, blunted or otherwise deformed by contact against the stringer.

From the foregoing compendium, it will be appreciated that an aspect of the present invention is to provide a cartridge for polymeric ligating clip of the general character described which is not subject to the aforementioned disadvantages of the antecedents of the invention.

A feature of the present invention is to provide a cartridge for polymeric ligating clip of the general character described which simple to use.

A consideration of the present invention is to provide a polymeric ligating clip cartridge of the general character described which assures that clips will be retained in their respective cartridge compartments for engagement by a clip applying instrument without damage.

Another aspect of the present invention is to provide a polymeric ligating clip cartridge of the general character described which assures the integrity of ribs or prongs on legs of a polymeric ligating clip.

A further feature of the present invention is to provide a polymeric ligating clip cartridge of the general character described which is well suited for economical mass production fabrication.

An additional consideration of the present invention is to provide a polymeric ligating clip cartridge of the general character described which assures that clips carried in the cartridge are ready for use.

To provide a polymeric ligating clip cartridge of the general character described which facilitates extraction of clips from the cartridge without damage is another feature of the present invention.

Other aspects, features and considerations of the present invention in part will be obvious and in part will be pointed out hereinafter.

With these ends in view, the invention finds embodiment in various combinations of elements, arrangements of parts and series of steps by which the above-mentioned aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

In the accompanying drawings, wherein one of the various possible exemplary embodiments of the invention is shown.

DESCRIPTION OF THE INVENTION

Figure 1:
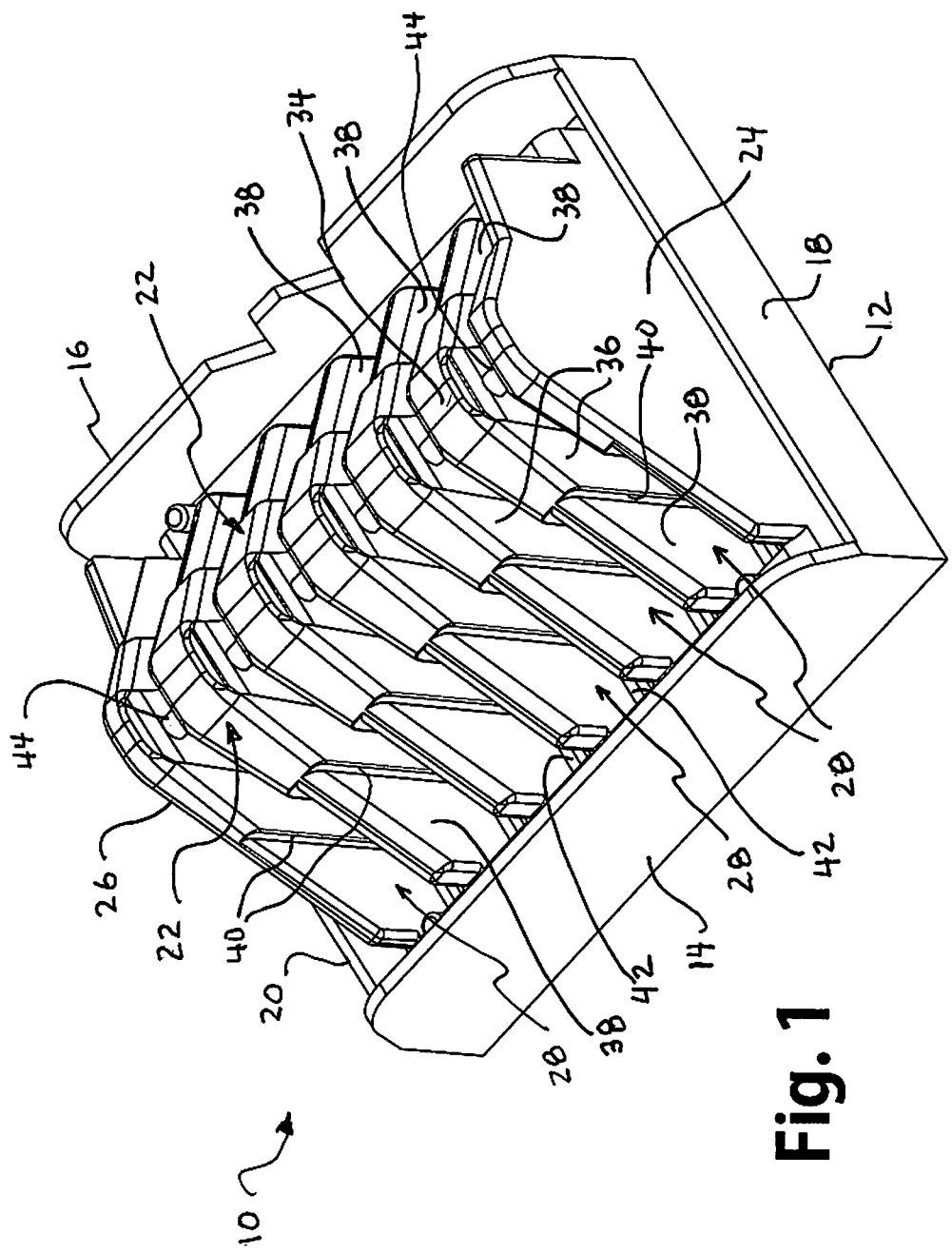
FIG. 1 is an isometric view of an improved clip cartridge in accordance with the present invention and showing a series of clip compartments formed by a plurality of parallel partitions.
Figure 2:
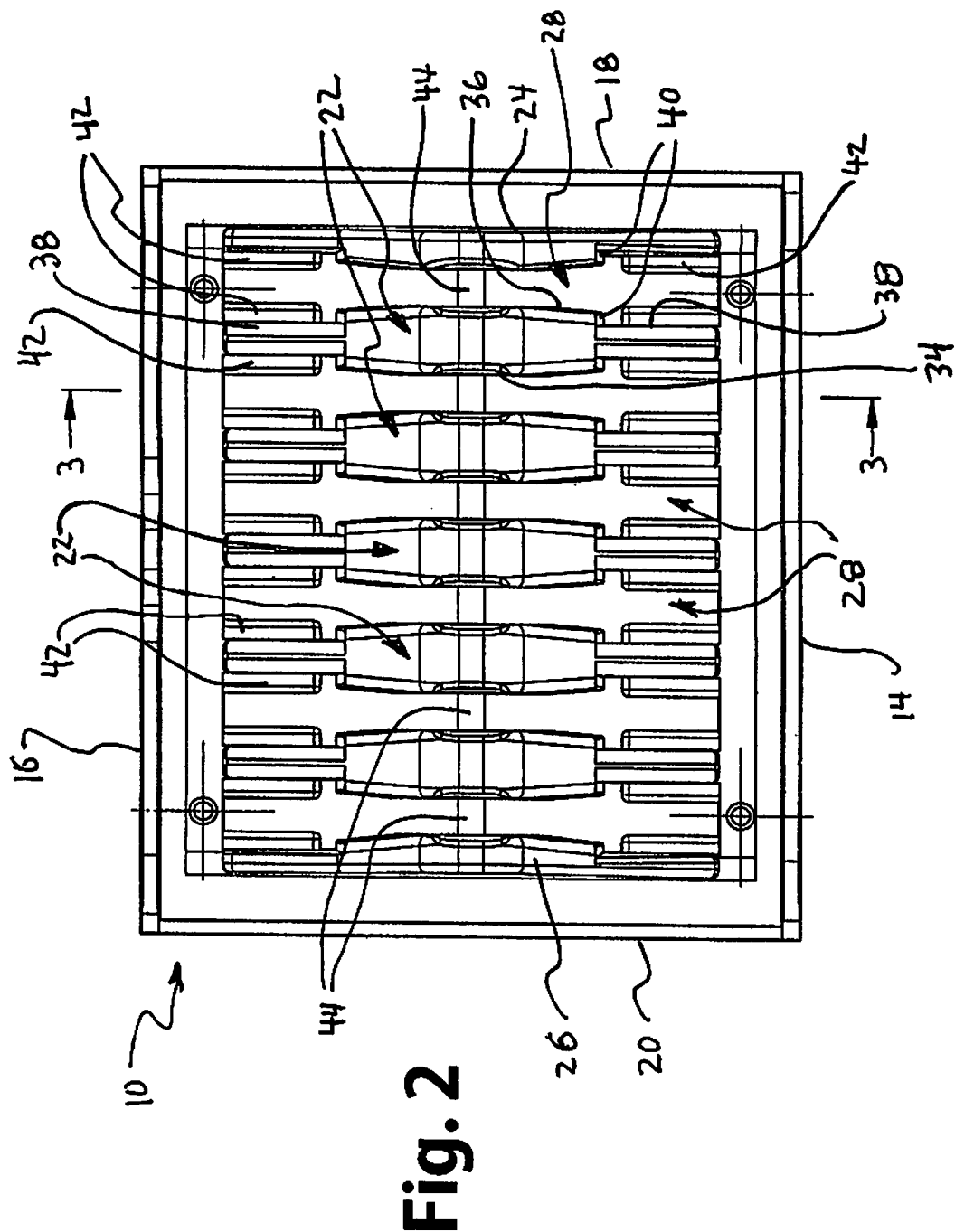
FIG. 2 is an enlarged scale top plan view of the cartridge.

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicants do not intend for any term in the specification or claims to be ascribed an uncommon or special meaning unless explicitly set forth as such. Further, the present invention encompasses present and future known equivalents to the known components referred to herein byway of illustration.

Referring now in detail to the drawings, the reference numeral 10 denoted generally a cartridge for ligating clips constructed in accordance with and embodying the invention. The cartridge 10 is formed with a rectangular base 12 having a pair of side walls 14, 16 and a pair of end walls 18, 20. A plurality of partitions 22, lying within evenly spaced parallel planes, are positioned within the base 12 between a pair of terminal partitions 24, 26. Opposed faces of adjacent partitions define compartments 28 which receive polymeric ligating clips 30, such as those disclosed in U.S. Pat. No. 10,265,079.

Figure 3:
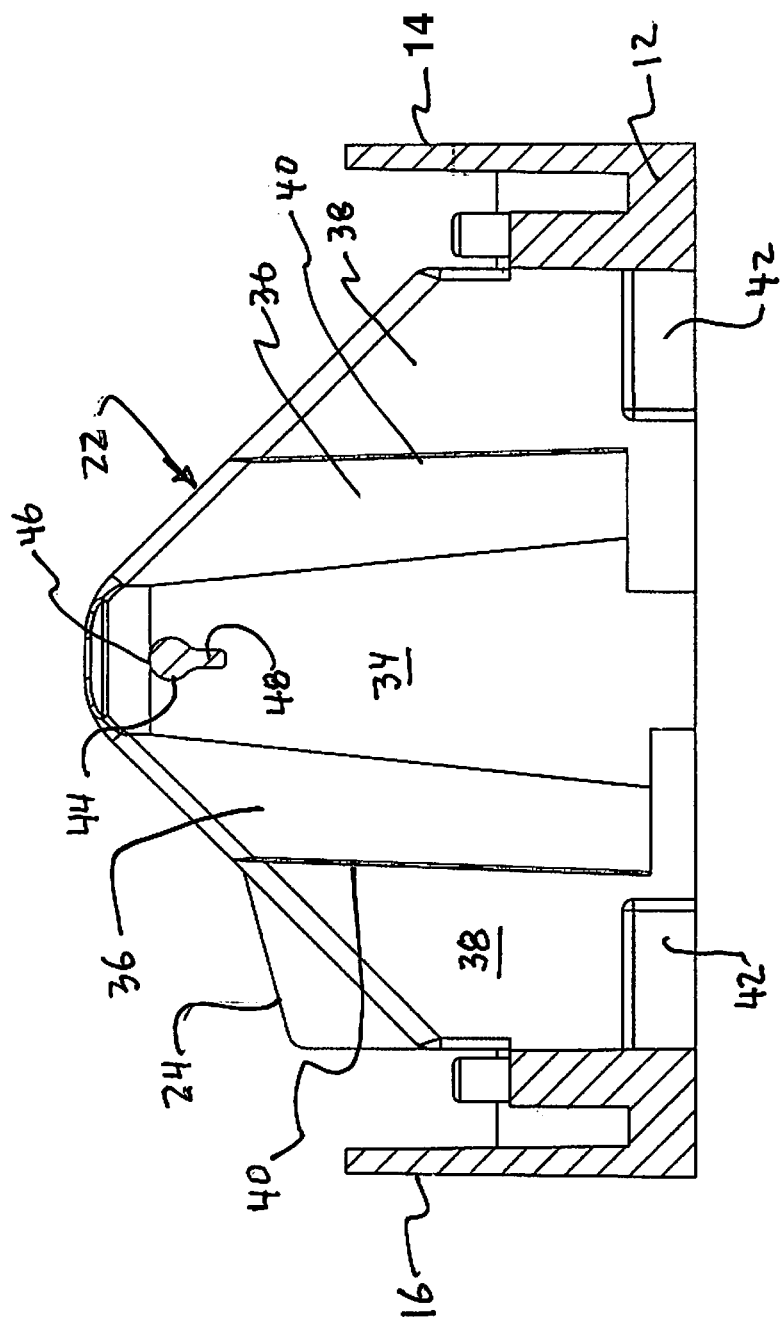
FIG. 3 is a sectional view through a cartridge compartment, the same taken along the plane 3-3 of FIG. 2 and showing a partition in elevation and a stringer which spans between opposed partitions.

With reference to FIG. 3, wherein the face of one partition 22 is depicted in elevation, it should be noted that the partition face includes a central face area 34 wherein the partition is thicker than the remaining portions of the partition. As such, the compartment space or zone between opposed central face areas 34 is narrowest. Extending laterally from the narrowest zone are intermediate zones formed between opposed face areas 36. The intermediate zones taper from the narrowest zone, at the junctures with the central face area 34, toward lateral face areas 38, wherein the partition 22 is of minimal thickness and the corresponding compartment space or zone is widest. Transitioning between each intermediate face area 36 and each lateral face area 38 is an abutment edge 40. Reinforcing support flanges 42 are formed at the base of the lateral face areas 38.

Figure 5:
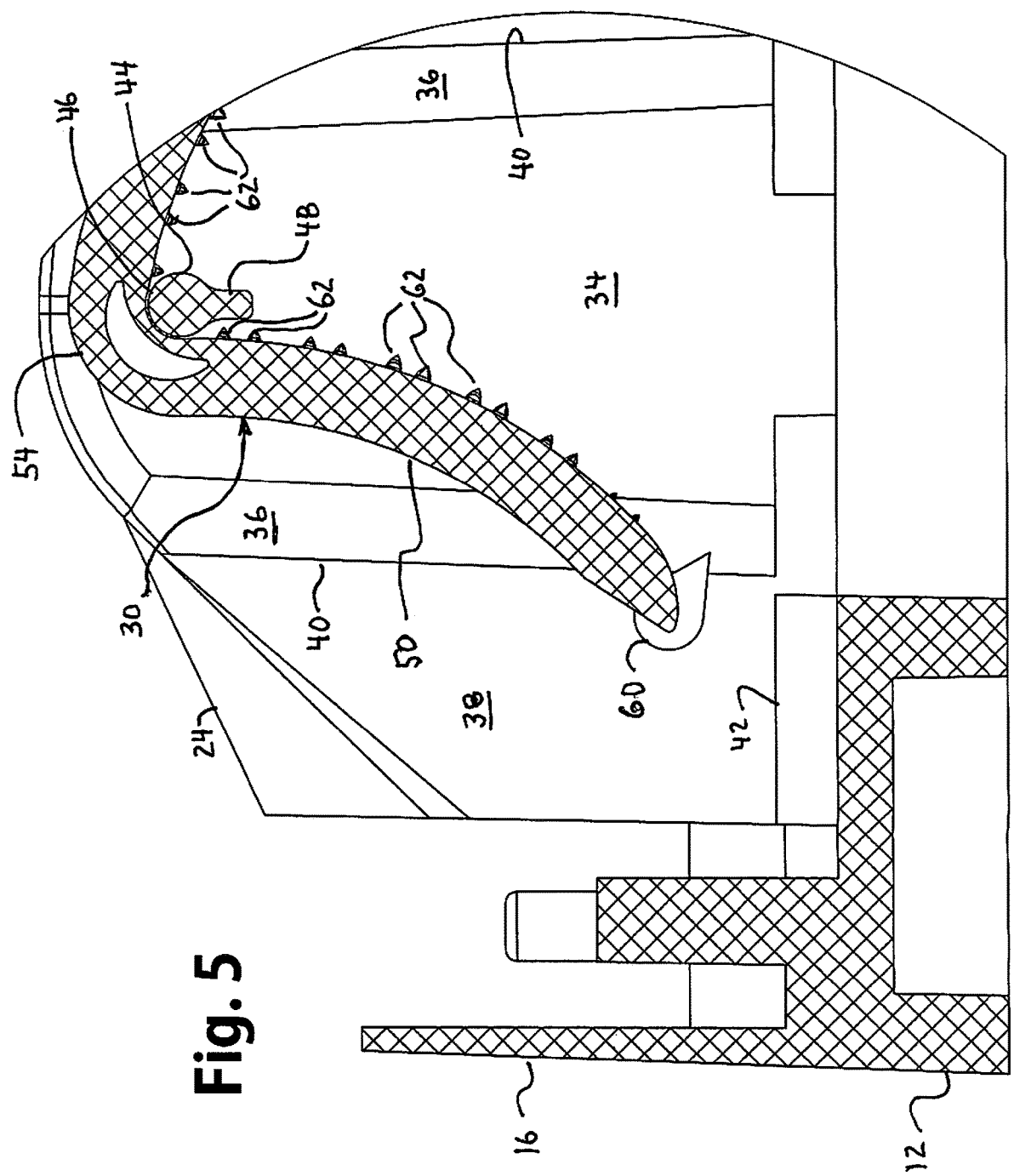
FIG. 5 is a greatly enlarged scale fragmentary cross sectional view through an unstressed clip seated within a compartment and suspended from the stringer and pivoted counter clockwise direction until a pair of bosses, at the end of a leg engages an abutment edge of the compartment.
Figure 6:
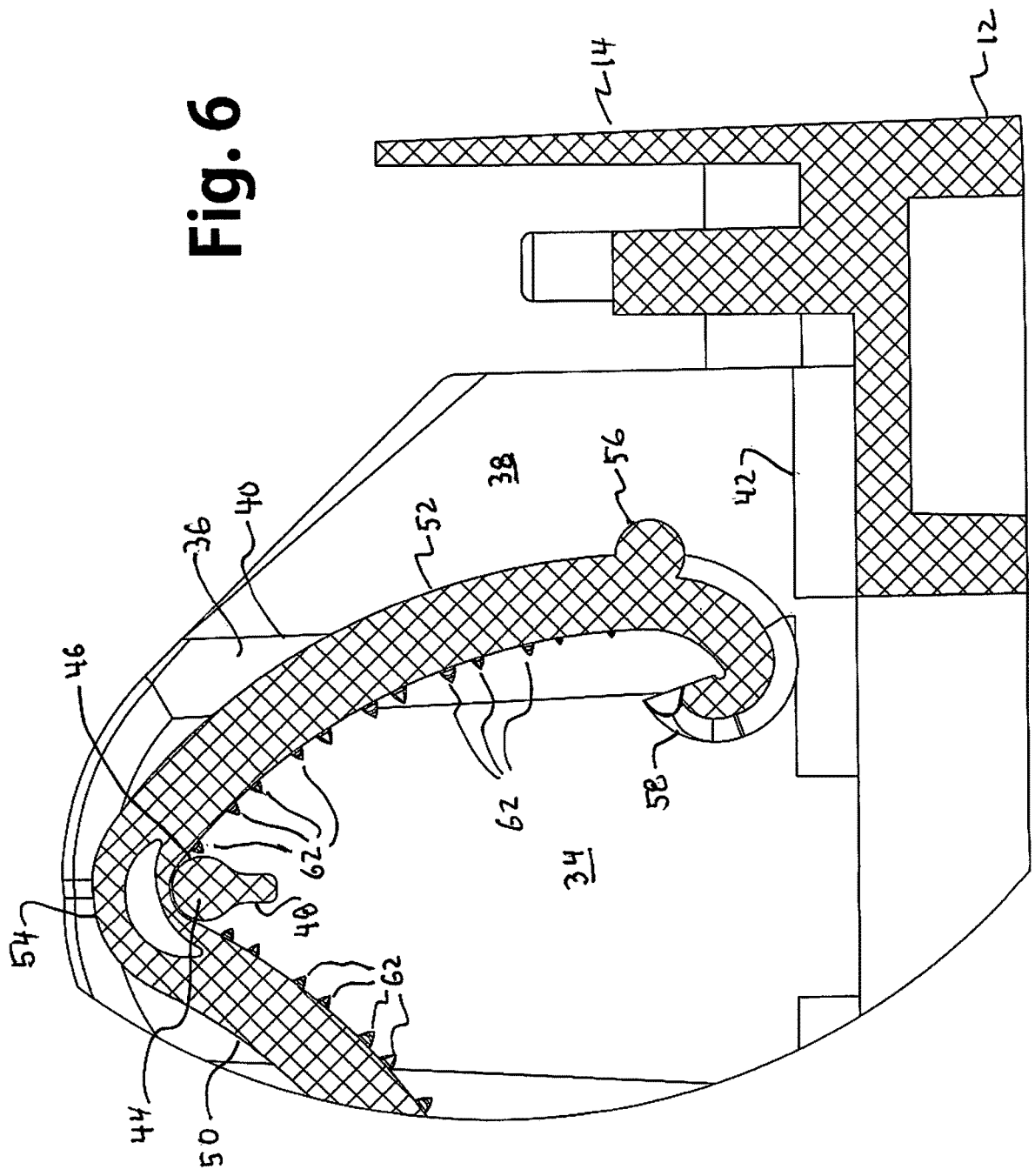
FIG. 6 is a greatly enlarged scale fragmentary cross sectional view through an unstressed clip seated within a compartment and suspended from the stringer and pivoted in a clockwise direction until a pair of bosses, at the end of a leg engages an abutment edge of the compartment.

Pursuant to the invention, a stringer 44 spans across each compartment 28 between opposed partitions 22. With reference to FIGS. 3, 5 and 6, the stringer comprises a substantially cylindrical body forming a crown surface 46 and a depending narrow support rib 48. The stringer 44 is thus configured in transverse cross section as being keyhole shaped, i.e., having a substantially cylindrical body and a depending vertical rib having parallel planar side walls projecting through an axial diametric plane of the cylinder.

Figure 4:
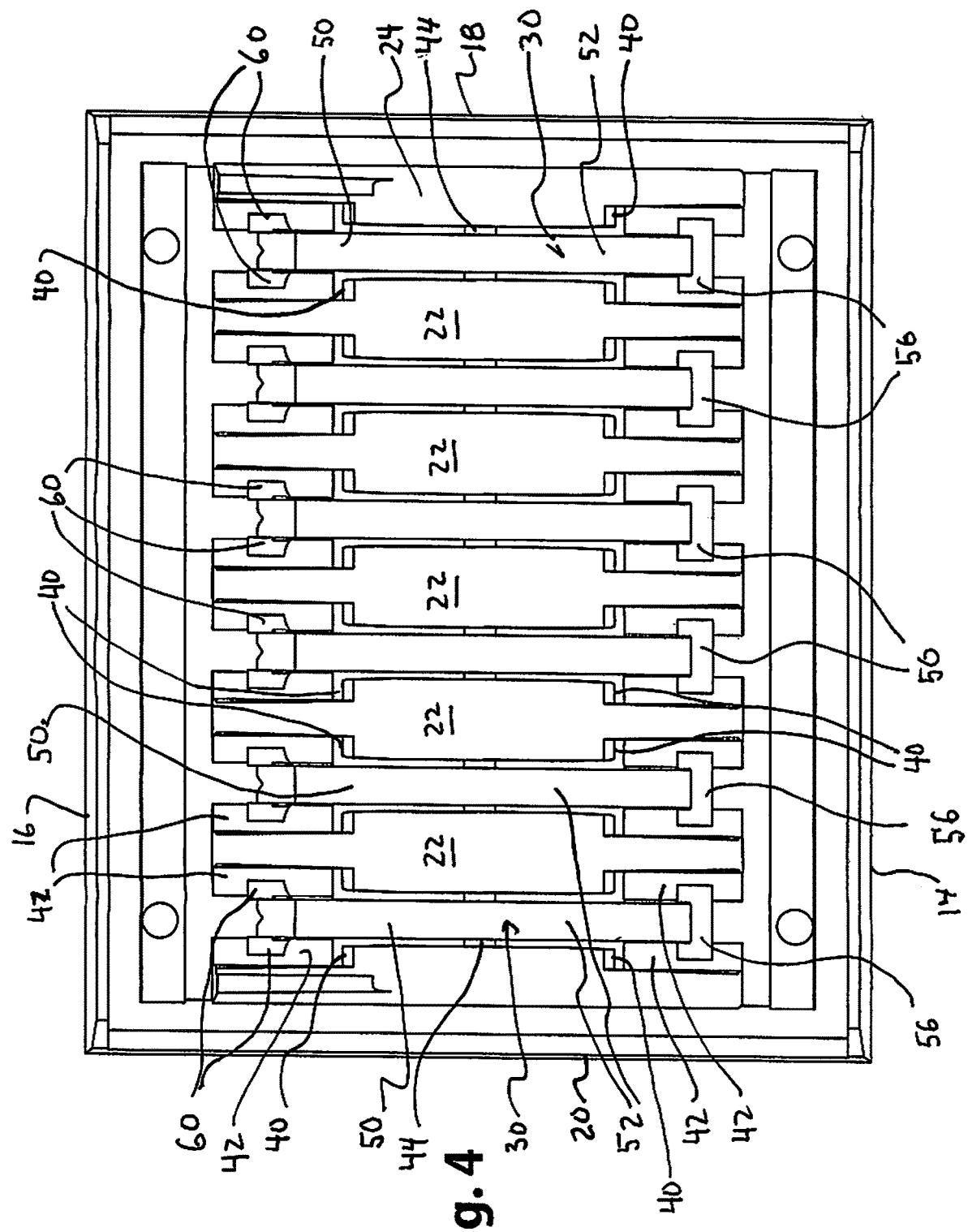
FIG. 4 is an enlarged scale top plan view of the cartridge loaded with unstressed clips.

The polymeric ligating clip 30 is illustrated in FIGS. 4, 5 and 6. The clip 30 comprises a pair of curved legs 50, 52 joined at an integral hinge 54. The leg 52 includes a lateral boss 56 adjacent a hook 58 and the other leg 50 incudes a pair of bosses 60 separated by a notch. On the interior face of each leg, rows of transverse ribs are provided, all as fully disclosed in U.S. Pat. No. 10,265,079.

Significantly, the stringer 44 is so dimensioned as to avoid contact with any of the ribs or prongs 62 when an unstressed clip is in its maximum counterclockwise position, depicted in FIG. 5 and when it is in its maximum clockwise position, depicted in FIG. 6. The maximum rotation positions are fixed by engagement between the bosses 56, 60 and the abutment edge 40. As illustrated in FIGS. 5 and 6, the total height of the stringer 44, from the top of the crown 46 to the bottom of the rib 48 is less than 20% of the length of the legs 50, 52 and thus sharply reduced surface area for potential rib or prong contact is available, as opposed to the prior art posts.

When the clips legs 50, 52 are bent toward one another about the hinge 54 by a clip applier instrument in order to remove a clip from the cartridge, (as illustrated in FIG. 11B of U.S. Pat. No. 6,880,699) engagement between the bosses 56, 60 and the abutment edge 40 precludes contact between the ribs or prongs and the stringer.

It should be appreciated that portions of the cartridge which may or may not appear in the drawings, such as the retainer element 250 and the retainer mounting post 151 of U.S. Pat. No. 6,880,699 and Publication No. 2019/0008521 A1 have not been described herein. For a complete disclosure thereof, reference is made to U.S. Pat. No. 6,880,699 and Publication No. 2019/0008521 A1, which are incorporated herein by reference.

In order to package or store a clip 30 in a compartment of the cartridge 10, the clip 30 is grasped adjacent the end of each leg by an instrument, e.g., a clip applier instrument or forceps; the clip is registered with the compartment and then placed in the compartment until the bosses 56, 60 seat within the lateral face areas 38, wherein the space between the opposed walls is widest. The instrument is then removed. After all of the clips have been placed, a retainer element is seated upon mounting posts to cover and retain the clips against dislodgment which might otherwise result from inadvertent inversion or tilting during shipment, etc.

Thus it will be seen that there is provided a cartridge for polymeric ligating clips which achieves the various aspects, features and considerations of the present invention and which is well suited to meet the conditions of practical usage.

In the figures of this application, in some instances, a plurality of elements may be shown as illustrative of a particular element, and a single element may be shown as illustrative of a plurality of particular elements. Showing a plurality of a particular element is not intended to imply that a system or method implemented in accordance with the invention must comprise more than one of that element or step, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs.

The particular combinations of elements and features in the above-detailed embodiment are exemplary only; the interchanging and substitution of these teachings with other teachings in this application are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc., are used for the sake of clarity. However the invention is not limited to the specific terms, numbers, dimensions, materials, etc. so selected, and each specific term, number, dimension, material, etc., at least includes all technical and functional equivalents that operate in a similar manner to accomplish a similar purpose.

Use of a given word, phrase, number, dimension, material, language terminology, product brand, etc. is intended to include all grammatical, literal, scientific, technical, and functional equivalents. The terminology used herein is for the purpose of description and not limitation.

Having described the preferred embodiment of the invention, it will now become apparent to one of ordinary skill in the art that other embodiments incorporating the concept may be used. Moreover, those of ordinary skill in the art will appreciate that the embodiment of the invention described herein can be modified to accommodate and/or comply with changes and improvements in the applicable technology and standards referred to herein.

Variations, modifications, and other implementations of what is described herein can occur to those of ordinary skill in the art without departing from the spirit and the scope of the invention.

Having thus described the Invention, there is claimed as new and desired to be secured by Letters Patent:

1. A polymeric ligating clip cartridge for at least one polymeric ligation clip having a pair of legs joined by a hinge, the cartridge including a base and at least one compartment, the at least one compartment comprising a pair of partition walls separated by a space and extending upwardly from the base, the cartridge further including a stringer spanning between the partition walls and across the space, the stringer being positioned above the base, the space being open between the stringer and the base, whereby the at least one polymeric ligation clip may be received within the at least one compartment and suspended from the stringer at the hinge.

2. The cartridge for polymeric ligation clips in accordance with claim 1 wherein the cartridge includes a plurality of compartments.

3. The cartridge for polymeric ligation clips in accordance with claim 2, the partition walls having central face areas wherein the space is narrowest and lateral face areas, wherein the space is widest and wherein the legs of a polymeric ligation clip will be free to move, the partition walls including intermediate face areas between the central face areas and the lateral face areas and an abutment for restraining movement of the legs, the abutment being positioned at the juncture between the lateral face areas and the intermediate face areas.

4. The cartridge for polymeric ligation clips in accordance with claim 3 further including a plurality of polymeric ligation clips, each having a pair of legs joined by a hinge, each leg having an inner face with a plurality of ribs or prongs, each polymeric ligation clip being received in a compartment with the hinge seated over the stringer, the ribs or prongs being so positioned and the stringer being so dimensioned as to avoid contact between the ribs or prongs and the stringer when the legs move within the widest space.

5. The cartridge for polymeric ligation clips in accordance with claim 3 wherein each leg includes a transverse boss, the legs being restrained by engagement between the abutment and the transverse boss.

6. The cartridge for polymeric ligation clips in accordance with claim 1 wherein the stringer comprises a substantially cylindrical body and a depending narrow support rib.

7. The cartridge for polymeric ligation clips in accordance with claim 1 the partition walls having central face areas, wherein the space is narrowest and lateral face areas, wherein the space is widest and wherein the legs of a polymeric ligation clip will be free to move.

8. The cartridge for polymeric ligation clips in accordance with claim 7 wherein the legs include inner faces having a plurality of ribs or prongs, the stringer being so dimensioned as to avoid contact with the ribs or prongs when the legs move within the widest.

9. The cartridge for polymeric ligation clips in accordance with claim 7 further including support flanges formed at a juncture of the base and the lateral face areas.

10. The cartridge for polymeric ligation clips in accordance with claim 7 wherein the polymeric ligation clips include transverse bosses at or adjacent the end of each leg, the bosses being positioned within areas wherein the space between the opposed walls is widest.

11. The cartridge for polymeric ligation clips in accordance with claim 7 the partition walls including an abutment for restraining movement of the legs, the partition walls further including intermediate face areas between the central face areas and the lateral face areas, the abutment being positioned at a juncture between the lateral face areas and the intermediate face areas.

12. A method of packing or storing at least one polymeric ligation clip having a pair of legs joined by a hinge, the method comprising the steps of:
 a) providing the cartridge as set forth in claim 1;
 b) grasping the at least one polymeric ligation clip with an instrument;
 c) registering the at least one polymeric ligation clip with the compartment;
 d) placing the at least one polymeric ligation clip into the compartment;
 e) removing the instrument;
 f) placing a retainer over the at least one polymeric ligation clip; and
 g) securing the retainer over the at least one polymeric ligation clip.

13. The method of packing or storing at least one polymeric ligation clip in accordance with claim 12 wherein a plurality of polymeric ligation clips are provided, the cartridge includes a plurality of compartments, steps b) through e) are performed for each polymeric ligation clip and the retainer is placed over the plurality of polymeric ligation clips.

14. A method of packing or storing at least one polymeric ligation clip in accordance with claim 12 wherein the at least one polymeric ligation clip includes bosses at or adjacent the end of each leg and step b) is performed by grasping the bosses.

15. A method of dispensing at least one polymeric ligation clip which has been packed or stored in accordance with steps a) through g) of claim 14, the method comprising the steps of h) removing the retainer; i) inserting the instrument into the at least one compartment; j) grasping the bosses with the instrument and; k) employing the instrument to remove the at least one polymeric ligation clip from the at least one compartment.

16. A cartridge for polymeric ligation clips having a pair of legs joined by a hinge, the legs having inner faces with a plurality of ribs or prongs, the cartridge having at least one compartment, the compartment comprising a pair of spaced partition walls extending upwardly from a base, the cartridge further including a stringer spanning between the partition walls, the stringer being positioned above the base the stringer being configured to support the polymeric ligation clip at the hinge, the height of the stringer being less than the length of the legs, whereby engagement between the ribs or prongs and the stringer is avoided.

17. The cartridge for polymeric ligation clips in accordance with claim 16 wherein the stringer is keyhole shaped in transverse cross section.

18. A cartridge for polymeric ligation clips having a pair of legs joined by a hinge, the legs having inner faces with a plurality of ribs or prongs, the cartridge having at least one compartment, the compartment comprising a pair of partitions extending along evenly spaced parallel planes, the cartridge further including a stringer spanning between the partitions, the stringer being configured to support the polymeric ligation clip at the hinge, the height of the stringer comprising no more than 20% of the length of the legs, whereby engagement between the ribs or prongs and the stringer is avoided.

19. The cartridge for polymeric ligation clips in accordance with claim 18 wherein the transverse cross section of the stringer is keyhole shaped.

20. The cartridge for polymeric ligation clips in accordance with claim 18 wherein the stringer comprises a substantially cylindrical body and a depending narrow support rib.

* * * * *